United States Patent [19]
Wei et al.

[11] Patent Number: 5,685,325
[45] Date of Patent: *Nov. 11, 1997

[54] DENTAL FLOSS HOLDER

[76] Inventors: Kuang-Hsing Wei; Kuang-Hung Wei, both of 18500 Bay Leaf Way, Germantown, Md. 20874

[*] Notice: The term of this patent shall not extend beyond the expiration date of Pat. No. 5,570,710.

[21] Appl. No.: 582,971

[22] Filed: Jan. 4, 1996

Related U.S. Application Data

[63] Continuation-in-part of Ser. No. 528,889, Sep. 15, 1995, Pat. No. 5,570,710, and Ser. No. 552,695, Nov. 3, 1995, abandoned.

[51] Int. Cl.$^6$ .................. A45D 2/00; A45D 2/38; A45D 2/46
[52] U.S. Cl. .................. 132/323; 132/326; 132/327; 132/329
[58] Field of Search .................. 132/321, 323, 132/324, 326, 327, 328, 329, 325

[56] References Cited

U.S. PATENT DOCUMENTS

| | | | |
|---|---|---|---|
| 4,050,470 | 9/1977 | Miller | 132/323 |
| 4,403,625 | 9/1983 | Sanders et al. | 132/323 |
| 4,638,824 | 1/1987 | De La Hoz | 132/323 |
| 5,435,330 | 7/1995 | Dix | 132/323 |
| 5,503,168 | 4/1996 | Wang | 132/323 |

*Primary Examiner*—Gene Mancene
*Assistant Examiner*—Pedro Philogene

[57] ABSTRACT

A dental floss holder for securely fastening one end of a dental floss instead of winding it around a finger includes a pair of jaws, two mating surfaces, and a locking member. The dental floss is retained between the jaws. One of the mating surfaces is formed on one jaw and the other mating surface on the other jaw. The locking member locks the jaws tightly such that there is substantially no gap or space between the mating surfaces so that the mating surfaces abut against each other closely to fasten the dental floss. The locking member and the jaws also comprise mating surfaces to be able to securely fasten the dental floss when the locking member locks both jaws.

37 Claims, 2 Drawing Sheets

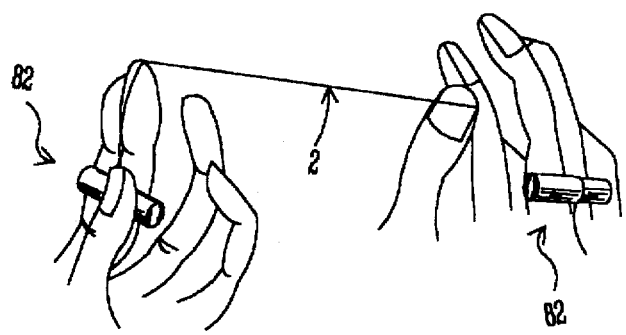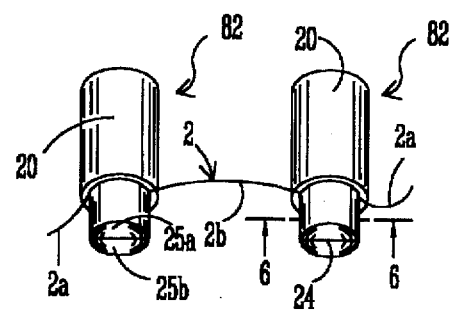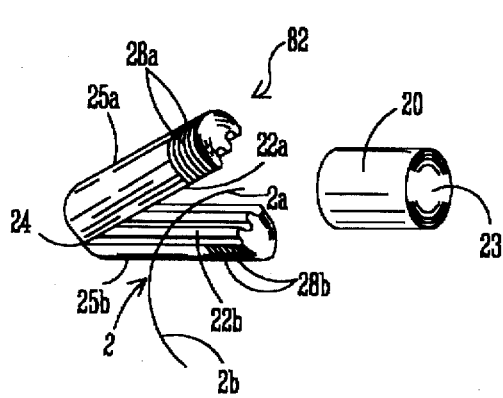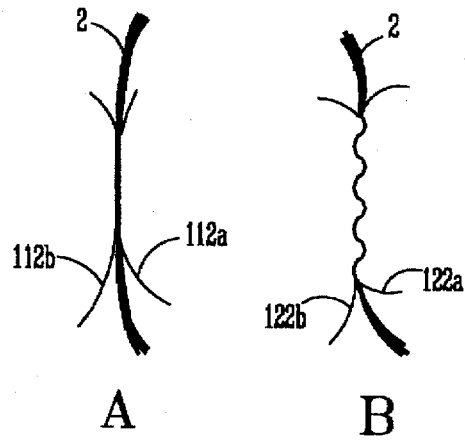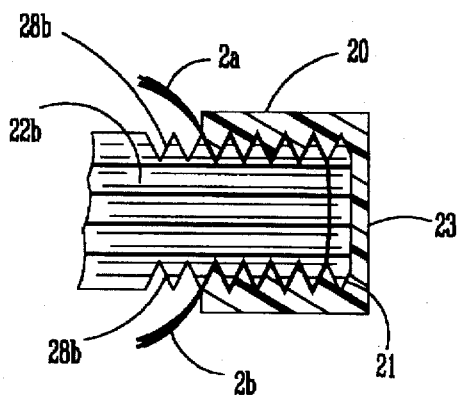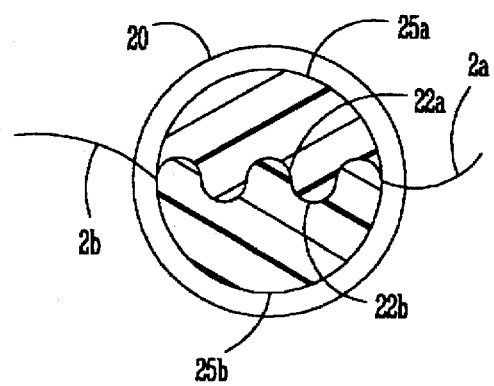

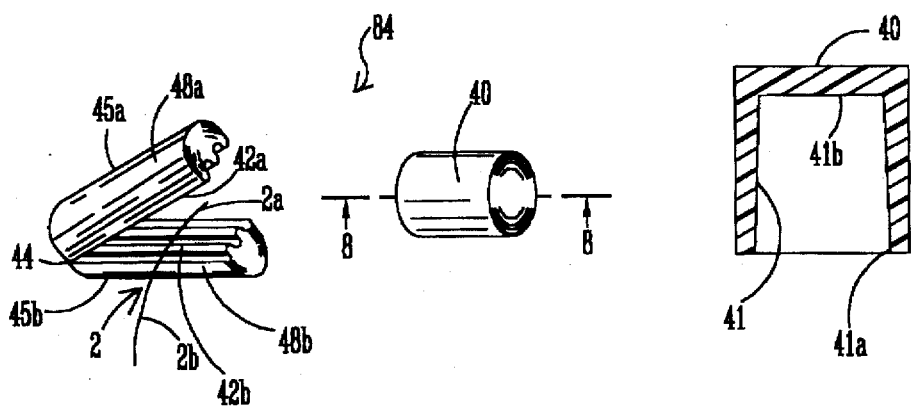
FIG. 7.
FIG. 8.
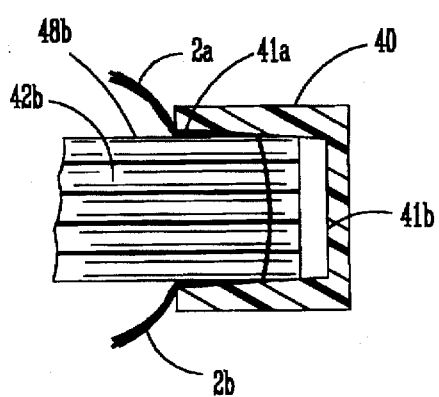
FIG. 9.
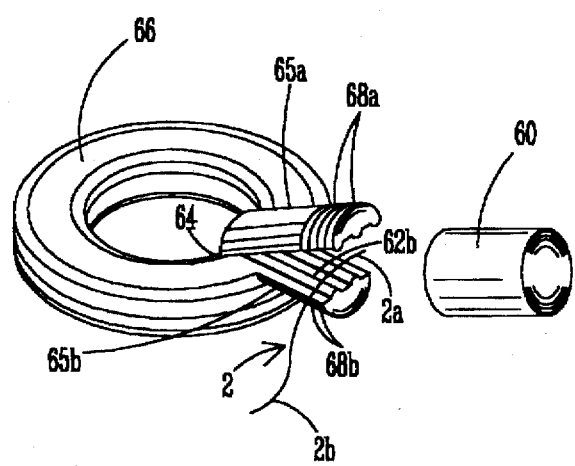
FIG. 10.
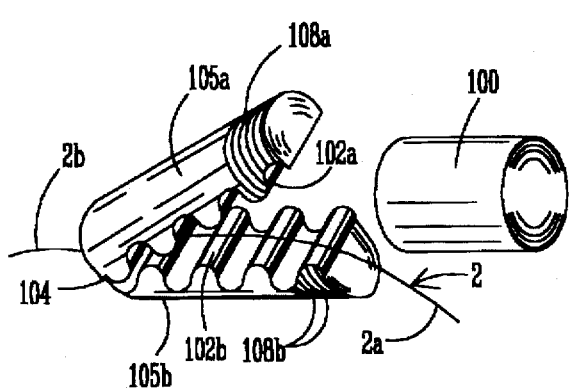
FIG. 11.
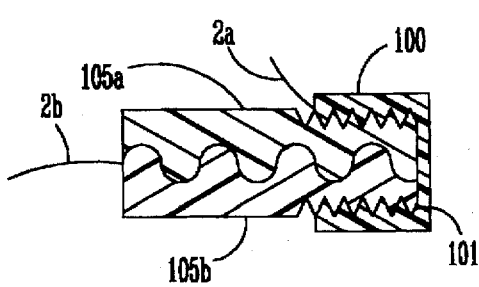
FIG. 12.

DENTAL FLOSS HOLDER

This is a CIP of application Ser. No. 08/528889 filed Sep. 15, 1995. Now U.S. Pat. No. 5,570,710 and application Ser. No. 08/552695 filed Nov. 3, 1995, now abandoned.

BACKGROUND OF THE INVENTION

Part 1. The Field of the Invention

This invention relates to the teeth cleaning with a length of dental floss and provides as its general object an improved device which is used to securely fasten dental floss and to render teeth-cleaning more effectively.

Part 2. Description of the Prior Art

There are many devices attempting to render flossing less tedious and make it more effective and convenient. Moreover, a growing number of dentists and orthodontists recommend highly for cleaning teeth daily by using dental floss to remove food particles between teeth. However, most people still don't floss daily, even those who take teeth-cleaning and dental care seriously. The inconvenience and discomfort for maneuvering the dental floss by winding ends of a length of dental floss around two fingers is the main reason. The winding ends of a length of dental floss around two fingers will not only cause discomfort on fingers but also render difficulties in manipulating in mouth. Although there are numerous devices with a predetermined length of floss fixed in two-pronged dental devices, maneuvering with two fingers winding a length of dental floss is still the most effective way of daily dental floss cleaning, especially for reaching and positioning between the rear most teeth, and is highly recommended by the dental profession. U.S. Pat. No. 4,050,470 to Miller (1977) provides a dental floss holder with an inwardly tapered slot extending along one elongate edge which does not fasten the dental floss securely in place to facilitate the manipulating of the floss in mouth. U.S. Pat. No. 4,638,824 to De La Hoz (1987) provides a pair of dental floss finger rings having three cut out prongs for retaining a length of dental floss. The retaining prongs are prone to cut the floss at the retaining point as a result of strong force applied during flossing. Also, the floss tends to be pull out of the prongs during flossing operation which requires different angles for inserting floss in between teeth at different positions.

SUMMARY OF THE INVENTION

It is a general object of the invention to provide a dental floss holder and a method for fastening one end of a dental floss. A dental floss holder for securely fastening one end of a dental floss instead of winding it around a finger includes a pair of jaws, two mating or corresponding surfaces, and a locking member. In the present invention, the dental floss is retained between the jaws. One of the mating surfaces is formed on one jaw and the other mating surface on the other jaw. The locking member locks the jaws tightly such that there is substantially no gap or space between the mating surfaces so that the mating surfaces abut against each other closely to fasten the dental floss. The locking member and the jaws also comprise mating surfaces to be able to securely fasten the dental floss when the locking member locks both jaws.

The method of the invention includes first retaining the dental floss between the jaws. It then follows with locking the jaws with the locking member so as to lock the jaws tightly together to securely, tightly fasten the dental floss between the mating surfaces.

Accordingly, several objects and advantages of the present invention are:

(a) to provide an improved dental floss holder which is used to eliminate the discomfort caused by winding a length of dental floss around fingers;

(b) to provide an improved dental floss holder which is designed to save the wasteful of floss for winding an extra length of dental floss around fingers;

(c) to provide an improved dental floss holder to securely fasten dental floss ends than wind around fingers which is needed to be rewound several times during the course of teeth-cleaning; and (d) to provide an improved dental floss holder to better control of a strained floss and perform a more effective teeth-cleaning.

Further objects and advantages of the invention will become apparent from the appended drawings and the ensuing specifications.

DRAWING FIGURES

FIG. 1 is a perspective view showing the use of the dental floss holders with a dental floss fastened on each holder;

FIG. 2 is a perspective view of the dental floss holders, shown in FIG. 1, connecting in pairs with a dental floss;

FIG. 3 is a perspective view of the dental floss holder;

FIG. 4 is an illustration of the principal of the invention;

FIG. 5 is a fragmentary sectional view showing details of a portion of the dental floss fastened in the dental floss holder of FIG. 2, taken on an enlarged scale for clarity.

FIG. 6 is a sectional elevation of the dental floss holder in position taken on the line 6—6 of FIG. 2;

FIG. 7 is a perspective view of an alternative embodiment of the dental floss holder;

FIG. 8 is a sectional elevation of the locking member in position taken on the line 8—8 of FIG. 7;

FIG. 9 is a fragmentary sectional view showing details of a portion of the dental floss fastened in the dental floss holder of FIG. 7 in a locked position, taken on an enlarged scale for clarity.

FIG. 10 is a perspective view of another alternative embodiment having the form of a ring formed on the dental floss holder;

FIG. 11 is a perspective view of another alternative embodiment of the dental floss holder; and FIG. 12 is a central longitudinal sectional elevation of the embodiment in FIG. 11 with jaws locked in a locking member.

DETAILED DESCRIPTION OF THE PREFERRED EMBODIMENT

Referring to FIGS. 1 and 2, it illustrates that a length of conventional dental floss 2 connects two identical dental floss holders 82. Dental floss 2 includes a section 2b and two sections 2a. Each section 2a defines each end of dental floss 2. Section 2b defines the portion of dental floss 2 between dental floss holders 82 and connects both holders 82. Each dental floss holder 82 is easily manipulated by each hand so that dental floss 2 is ready to be used inside mouth to clean teeth (not shown) as one usually does with both ends of a dental floss winding around fingers. One of dental floss holders 82 may be held by one hand (left in FIG. 1) and the other holder may be supported by the back of the other hand (right in FIG. 1) to clean teeth. Dental floss holders 82 provide much better control of dental floss 2 and eliminate the discomfort by winding ends of a dental floss around fingers. A single holder may be used on one hand with the opposite end of the dental floss fastened by some other means or by fingers; however, it is expected that two holders will be used. Dental floss holder 82 is suitable for use with the conventional thread or cord type of dental floss or with ribbon or band type of floss. It should be understood that the term "dental floss" is used generically to indicate any type of floss.

Referring now to FIGS. 2 and 3 each dental floss holder 82 comprises retaining means for retaining each end of dental floss 2. In the preferred form of the present invention the retaining means comprises a first jaw 25a and a second jaw 25b. Each jaw preferably comprises a substantially elongated semicircular piece of material or one half of a circular cylinder dimensioned to be easily handled by fingers when retaining dental floss 2 between jaws 25a and 25b. Each dental floss holder 82 also comprises joining means for joining jaws 25a and 25b at one end. In the illustrated form of the invention the joining means comprises a hinged join 24 which can be easily flipped open and close of jaws 25a and 25b. It is understood that any other form of the joining means, such as a springable join or a pivoted join, will suffice the present invention. It is also workable in the present invention even when jaws 25a and 25b are not joined together at all at one end, that is, jaws 25a and 25b are separated pieces.

Referring particularly to FIGS. 3, 4, and 6, each dental floss holder 82 further comprises first fastening means for fastening dental floss 2. The first fastening means defines two surfaces having mating or corresponding dimensions such that when both surfaces abut against each other, there is substantially no gap or space therebetween so that dental floss 2 is fastened therebetween. In this form of the invention the first fastening means comprises a first internal surface 22a and a second internal surface 22b. Internal surface 22a and internal surface 22b are configured to have mating or corresponding dimensions so that when both surfaces are matingly joined, internal surface 22a and internal surface 22b abut against each other to fit tightly together without substantially any gap or space therebetween so as to securely fasten dental floss 2 therebetween. Internal surfaces 22a and 22b also comprise the form of small mating ridges or corrugations integrally longitudinally formed thereon to facilitate the fastening of dental floss 2 (FIG. 6). Dental floss 2 is placed transversely across internal surface 22a and internal surface 22b having sections 2a and 2b on either side (FIG. 3) so that dental floss 2 can be effectively securely fastened therebetween. In the illustrated form of the invention internal surfaces 22a and 22b are preferably integrally formed substantially on the diameters of the semicircles of the external peripheral surfaces of jaws 25a and 25b, respectively. The longitudinal lengths of internal surfaces 22a and 22b formed on the external peripheral surfaces of jaws 25a and 25b are preferably substantially equal to the longitudinal lengths of jaws 25a and 25b, respectively. The principal of the invention for fastening one end of dental floss 2 between mating surfaces is best shown in FIG. 4. As seen in A of FIG. 4, dental floss 2 is securely fastened between a surface 112a and a surface 112b. Surfaces 112a and 112b are configured to have mating or corresponding dimensions so that when both surfaces are matingly joined, surface 112a and surface 112b abut against each other tightly. The engagement or abutment between surfaces 112a and 112b is sufficiently tight such that there is substantially no gap or space therebetween. The length of the engagement is preferably substantially equal to one-eighth of an inch in this form of the invention. Other lengths of engagement may, of course, be used as required. When dental floss 2 is fastened between the engagement, the cross-sectional dimension of dental floss 2 is then tightly compressed or flattened between surfaces 112a and 112b. Therefore, the closely abutted surfaces 112a and 112b are to effectively clamp the compressed dental floss 2 and to securely fasten dental floss 2 therebetween. Also, as seen in B of FIG. 4, a surface 122a and a surface 122b have the same fastening function that surfaces 112a and 112b have, except that surfaces 122a and 122b comprise the form of small mating ridges or corrugations or screw threads.

Referring to FIGS. 2, 3, and 5, each dental floss holder 82 also comprises locking means for locking the first fastening means together so that dental floss 2 is securely fastened. In the preferred form of the invention the locking means comprises a first outer surface 28a, a second outer surface 28b, an inner surface 21, and a locking member 20. Locking member 20 comprises preferably substantially an elongated cylindrical piece of material and is also dimensioned to be easily handled by fingers. Preferably, locking member 20 has an end 23 defining a closed end of locking member 20. Inner surface 21 is preferably integrally formed on the internal peripheral surface of locking member 20 (FIG. 5). Also, inner surface 21 is configured generally to have a diameter substantially uniform throughout its length. In the illustrated form of the invention outer surfaces 28a and 28b are preferably integrally formed substantially on the arcs of 180° of the semicircles of the external peripheral surfaces of jaws 25a and 25b, respectively. The longitudinal lengths of outer surfaces 28a and 28b formed on the external peripheral surfaces of jaws 25a and 25b are preferably substantially equal to the longitudinal lengths of jaws 25a and 25b, respectively. When outer surface 28a closes up or combines with outer surface 28b, the closed or combined outer surfaces 28a and 28b comprises a combined diameter substantially uniform throughout the length of the combined configuration. Outer surfaces 28a and 28b comprise the form of screw threads. Also, inner surface 21 comprises the form of screw threads. Outer surfaces 28a and 28b are dimensioned such that when jaws 25a and 25b close up or combine together, inner surface 21 is able to screw together with outer surfaces 28a and 28b so as to securely lock jaws 25a and 25b together so that dental floss 2 is securely fastened between mating internal surfaces 22a and 22b.

Referring still to FIGS. 2, 3, and 5, each dental floss holder 82 further comprises second fastening means for further fastening dental floss 2 after fastened in the first fastening means. In this form of the invention the second fastening means comprises first outer surface 28a, second outer surface 28b, and inner surface 21. As inner surface 21 proceeds longitudinally toward the closed jaws 25a and 25b, inner surface 21 abuts against outer surfaces 28a and 28b. Inner surface 21 and outer surfaces 28a and 28b are dimensioned such that the engagement or abutment between inner surface 21 and outer surfaces 28a and 28b creates substantially no gap or space therebetween. The engagement creates the fastening function described in B of FIG. 4 of the principal of the invention. Because inner surface 21 abuts against outer surfaces 28a and 28b to fit tightly together without substantially any gap or space therebetween, dental floss 2 is then securely fastened therebetween. Inner surface 21 may stop the forward movement when it comes into contact with end 23. It is understood that retaining dental floss 2 substantially near the opposite end of join 24 will increase the lengths of engagement between inner surface 21 and outer surfaces 28a and 28b. Also, it is understood that applying both the first fastening means and the second fastening means to fasten one end of dental floss 2 is preferred in the present invention. However, when one end of dental floss 2 is retained substantially transversely between jaws 25a and 25b substantially near join 24, the engagement between inner surface 21 and outer surfaces 28a and 28b may not engage with dental floss 2 at all. Also, when locking member 20 is relatively short to cover only small portion of jaws 25a and 25b, the engagement between inner surface 21 and outer surfaces 28a and 28b may again not engage with dental floss 2 at all. Consequently, the first fastening means is used alone without the assistance of the second fastening means to fasten one end of dental floss 2. However, using both the first and second fastening means is preferred. Therefore, it is understood that locking member 20 may be made sufficiently long to cover jaws 25a and 25b.

Based on the same principal of the invention, referring now to FIGS. 7 and 8, a dental floss holder 84 is substantially similar to dental floss holder 82 (FIG. 3) in structure and in operation. Dental floss holders 84 and 82 achieve exactly the same resultant effects. Dental floss holder 84 still comprises the same retaining means that dental floss holder 82 has for retaining one end of dental floss 2. In the preferred form of the present invention the retaining means comprises a first jaw 45a and a second jaw 45b. First jaw 45a and second jaw 45b are identical to first jaw 25a and second jaw 25b, respectively. Jaws 45a and 45b also preferably comprise generally elongated semicircular pieces of material dimensioned to be easily handled by fingers when retaining dental floss 2 between jaws 45a and 45b. Dental floss holder 84 also comprises the same joining means that dental floss holder 82 has for joining both jaws 45a and 45b at one end. In the illustrated form of the invention the joining means comprises a hinged join 44. Join 44 is identical to join 24 in structure, in operation and in resultant effects. Dental floss holder 84 also comprises the same first fastening means that dental floss holder 82 has. The first fastening means has been defined as two surfaces having mating dimensions for fastening dental floss 2 therebetween. In this form of the invention the first fastening means comprises a first internal surface 42a and a second internal surface 42b. Internal surface 42a and internal surface 42b are identical to internal surface 22a and internal surface 22b, respectively, in structure, in operation and in resultant effects.

Referring to FIGS. 7, 8, and 9, dental floss holder 84 also comprises substantially the same locking means that dental floss holder 82 has for locking the first fastening means together so that dental floss 2 is securely fastened. In the preferred form of the invention the locking means comprises a first outer surface 48a, a second outer surface 48b, an inner surface 41, and a locking member 40. Locking member 40 comprises preferably substantially an elongated cylindrical piece of material and is also dimensioned to be easily handled by fingers. Inner surface 41 is preferably integrally formed on the internal peripheral surface of locking member 40. Also, inner surface 41 preferably comprises substantially the form of a frustum having a larger diameter end 41a and a smaller diameter end 41b. In the illustrated form of the invention outer surfaces 48a and 48b are preferably integrally formed on the arcs of 180° of the semicircles of the external peripheral surfaces of jaws 45a and 45b, respectively. The longitudinal lengths of outer surfaces 48a and 48b formed on the external peripheral surfaces of jaws 45a and 45b are preferably substantially equal to the longitudinal lengths of jaws 45a and 45b, respectively. The dimensions of outer surfaces 48a and 48b are such that when jaws 45a and 45b are closed or combined together, outer surfaces 48a and 48b form a substantially cylindrical configuration having a substantially uniform diameter throughout the length of the closed or combined cylindrical configuration. The diameter of the combined outer surfaces 48a and 48b is slightly smaller than the diameter of end 41a and slightly larger than the diameter of end 41b. Therefore, when locking member 40 connects inner surface 41 with combined outer surfaces 48a and 48b, end 41a will allow the insertion of the combined outer surfaces 48a and 48b into inner surface 41. As outer surfaces 48a and 48b proceed longitudinally a distance (preferably about one-third the longitudinal length of outer surface 48a or 48b) into inner surface 41 to a position where the diameter of the combined outer surfaces 48a and 48b is substantially equal to that of inner surface 41, outer surfaces 48a and 48b come into contact with inner surface 41. The insertion movement of outer surfaces 48a and 48b are restricted by inner surface 41. Inner surface 41 and outer surfaces 48a and 48b comprise any suitable materials having resilient character such as plastic and metal. Also, both jaws 45a and 45b and locking member 40 comprise any rigid materials. In this form of the invention inner surface 41 is preferably integrally formed on the internal peripheral surface of locking member 40. Also, outer surfaces 48a and 48b are preferably integrally formed on the external peripheral surfaces of jaws 45a and 45b, respectively. Therefore, outer surfaces 48a and 48b can still further proceed toward end 41b upon applying an additional force such as a push. However, jaws 45a and 45b and locking member 40 add frictional engagement between inner surface 41 and outer surfaces 48a and 48b. The frictional engagement between inner surface 41 and outer surfaces 48a and 48b creates substantially no gap or space therebetween whereby dental floss 2 is effectively, securely fastened between inner surface 41 and outer surfaces 48a and 48b.

Referring now particularly to FIG. 9, dental floss holder 84 still comprises substantially the same second fastening means that dental floss holder 82 has for further fastening dental floss 2 after fastened in the first fastening means. In this form of the invention the second fastening means comprises first outer surface 48a, second outer surface 48b, and inner surface 41. Inner surface 41 and outer surfaces 48a and 48b are dimensioned such that the engagement or abutment creates substantially no gap or space therebetween. The engagement creates the fastening function described in A of FIG. 4 of the principal of the invention. Because inner surface 41 abuts against outer surfaces 48a and 48b to fit tightly together without substantially any gap or space between inner surface 41 and outer surfaces 48a and 48b, dental floss 2 is then securely fastened therebetween. As inner surface 41 comes into contact with outer surfaces 48a and 48b, the further push of outer surfaces 48a and 48b into inner surface 41 will create frictional engagement so that dental floss 2 is extremely tightly fastened between inner surface 41 and outer surfaces 48a and 48b.

The method of fastening one end of dental floss 2 according to the invention may be best described with reference to FIGS. 2, 3, and 5. The method includes first retaining one end of dental floss 2 substantially transversely between jaws 25a and 25b near the opposite end of join 24 with section 2a on one side of jaws 25a and 25b and section 2b on the other side of jaws 25a and 25b. Therefore, dental floss 2 extends from section 2a on one side of jaws 25a and 25b, reaches substantially transversely between jaws 25a and 25b to the other side of jaws 25a and 25b to section 2b. In the illustrated preferred form of the invention, mating internal surfaces 22a and 22b are formed on the diameters of the semicircles of the external peripheral surfaces of jaws 25a and 25b, respectively. Therefore, when dental floss 2 is substantially transversely retained between jaws 25a and 25b having sections 2a and 2b on either side of jaws 25a and 25b, sections 2a and 2b must also be on either side of internal surfaces 22a and 22b.

Having dental floss 2 retained between jaws 25a and 25b with sections 2a and 2b on either side of jaws 25a and 25b, the method continues with the step of locking jaws 25a and 25b tightly together such that internal surfaces 22a and 22b are tightly locked together without substantially any gap or space therebetween so that dental floss 2 is securely, tightly fastened between internal surfaces 22a and 22b. In the illustrated form of the invention internal surfaces 22a and 22b have mating dimensions to be able to abut against each other tightly without substantially any gap or space therebetween so as to securely fasten dental floss 2.

The preferred method of fastening one end of dental floss 2 also includes the step of further fastening dental floss 2 between inner surface 21 and outer surfaces 28a and 28b after locking jaws 25a and 25b to fasten dental floss 2 between internal surfaces 22a and 22b. In the illustrated form of the invention inner surface 21 is formed on the internal peripheral surface of locking member 20. Also, outer surfaces 28a and 28b are formed on the external peripheral surfaces of jaws 25a and 25b, respectively. Inner surface 21 and outer surfaces 28a and 28b have mating dimensions to be able to abut against each other tightly without substantially any gap or space therebetween so as to securely fasten dental floss 2.

FIG. 10 illustrates another embodiment similar to that of FIG. 3, except that a second jaw 65b comprises substantially the form of a ring. A ring 66 is adapted to fit a finger so that ring 66 may be inserted into a finger when cleaning teeth. A join 64 which is identical to join 24 is also provided for joining second jaw 65b with a first jaw 65a. Ring 66 is preferably integrally formed on jaw 65b at a position near join 64 so that ring 66 will not prevent the forward movement of a locking member 60 locking jaws 65a and 65b together to fasten dental floss 2. Locking member 60 comprises preferably a substantially cylindrical piece of material. FIG. 10 shows that jaw 65a or jaw 65b may comprise substantially the form of a ring. Similarly, locking member 60 may also comprise substantially the form of a ring as required. It is understood that any general, suitable piece of materials having any suitable shapes such as a cylinder and a ring dimensioned to be handled by fingers may be used. It is also understood that the form of a ring or any suitable configurations may be formed substantially on locking member 60 or jaw 65a or jaw 65b. Otherwise, the embodiment of FIG. 10 is substantially identical to that of FIG. 3 in operation, in resultant effects and substantially in structure.

FIG. 11 illustrates a further embodiment similar to that of FIG. 3, except that a first internal surface 102a and a second internal surface 102b have mating small ridges or corrugations substantially integrally transversely formed thereon rather than substantially longitudinally formed on internal surfaces 22a and 22b (FIG. 3). The embodiment of FIG. 11 comprises an inner surface 101 (FIG. 12) which is identical to inner surface 21. The embodiment of FIG. 11 also comprises a first outer surface 108a and a second outer surface 108b which are identical to outer surfaces 28a and 28b, respectively. Inner surface 101 and outer surfaces 108a and 108b are also dimensioned to be able to abut together to fasten dental floss 2. The embodiment of FIG. 11 also includes a join 104 which is identical to join 24. In operation, the method of fastening one end of dental floss 2 includes retaining one end of dental floss 2 substantially longitudinally between jaws 105a and 105b with section 2a substantially near the opposite end of join 104 and section 2b extending out from substantially near join 104. Therefore, section 2a extends substantially from near the opposite end of join 104, reaches substantially longitudinally between jaws 105a and 105b to join 104, and extends out substantially from near join 104 to section 2b. The method continues with the step of locking jaws 105a and 105b to fasten dental floss 2 between internal surfaces 102a and 102b. The method also continues with the step of fastening dental floss 2 between inner surface 101 and outer surface 108a or 108b. The steps of locking jaws 105a and 105b, and fastening dental floss 2 between inner and outer surfaces are substantially identical to the steps described above for dental floss holder 82. When section 2a extends from outside jaws 105a and 105b near the opposite end of join 104 through substantially longitudinally between jaws 105a and 105b to section 2b, sectional 2b will extend out from near join 104 and sectional 2a will extend out from the opposite end of join 104. Therefore, when a locking member 100 locks together jaws 105a and 105b, dental floss 2 is fastened between internal surfaces 102a and 102b. As locking member 100 proceeds toward join 104 to lock jaws 105a and 105b, inner surface 101 abuts against outer surfaces 108a and 108b; therefore, section 2a is also fastened between inner surface 101 and outer surface 108a or 108b (FIG. 12). When section 2a extends from inside jaws 105a and 105b near the opposite end of join 104 through substantially longitudinally between jaws 105a and 105b to section 2b, dental floss 2 is fastened between internal surfaces 102a and 102b only. The embodiment of FIG. 11 is substantially identical to that of FIG. 3 in operation, in resultant effects and substantially in structure.

Although the description above contains many specifications, these should not be construed as limiting the scope of the invention but as merely providing illustrations of some of the presently preferred embodiments of this invention. Thus the scope of the invention should be determined by the appended claims and their legal equivalents, rather than by the examples given.

We claim:

1. A dental floss holder for fastening one end of a dental floss, said holder comprising:

a first jaw having a first internal surface thereon;

a second jaw having a second internal surface thereon, each of said jaws adapted to be handled by fingers, whereby said jaws may be held by fingers to facilitate the retention of the floss, said surfaces being engageable to abut against each other such that the floss is fastened between said surfaces, whereby the floss is fastened in a manner selected from a range from substantially longitudinally therebetween to substantially transversely therebetween; and locking means for locking said jaws together so that when said jaws are locked together by said locking means, the floss is fastened between said surfaces, whereby when the floss is fastened between said surfaces, said holder having the floss fastened therein is manipulated by a hand in lieu of winding the floss around a finger for teeth cleaning.

2. The holder of claim 1, further comprising second fastening means for fastening the floss therein so that when said jaws are locked together by said locking means, the floss is fastened in said surfaces and in said second fastening means.

3. The holder of claim 2, wherein said locking means comprises a locking member, an inner surface, and two separate outer surfaces, said second fastening means including said inner surface and said outer surfaces, said inner surface formed on said locking member, one of said outer surfaces formed on one of said jaws and the other of said outer surfaces formed on the other of said jaws, said outer surfaces combined together being engageable with said inner surface to lock said jaws so that the floss is fastened between said inner surface and at least one of said outer surfaces.

4. The holder of claim 3, wherein said inner surface is a threaded surface and said outer surfaces combined together form a threaded surface.

5. The holder of claim 3, wherein said inner surface is a generally frustum surface and said outer surfaces combined together form a generally uniform surface.

6. The holder of claim 1, wherein said locking means comprises a locking member, an inner surface, and two separate outer surfaces, said inner surface formed on said locking member, one of said outer surfaces formed on one of said jaws and the other of said outer surfaces formed on the other of said jaws, said outer surfaces combined together being engageable with said inner surface to lock said jaws.

7. The holder of claim 1, wherein at least one of said internal surfaces further comprises corrugations formed thereon.

8. The holder of claim 1, wherein each of said jaws comprises a substantially elongated generally semicircular configuration.

9. The holder of claim 1, wherein at least one of said first jaw, said second jaw, and said locking means comprises a substantially ring-shaped configuration adapted to be fitted into a finger.

10. The holder of claim 1, wherein said locking means comprises a locking member having a generally elongated configuration, such as a cylindrical configuration, adapted to be handled by fingers.

11. The holder of claim 1, further comprising joining means for joining said jaws at one end thereof.

12. The holder of claim 1, wherein said joining means comprises any one of the following configurations selected from the group consisting of a hinged join, a springable join, and a pivoted join.

13. A dental floss holder for fastening one end of a dental floss, said holder comprising:
a first jaw;
a second jaw, each of said jaws adapted to be handled by fingers, whereby said jaws may be held by fingers to facilitate the retention of the floss;
two internal surfaces, one of said surfaces formed on said first jaw and the other of said surfaces formed on said second jaw, said surfaces being engageable to abut against each other to fasten the floss therebetween, whereby the floss is fastened in a manner including at least one of the following: substantially longitudinally therebetween and substantially transversely therebetween; and
locking means for locking said jaws together so that when said jaws are locked together by said locking means, the floss is fastened between said surfaces, whereby when the floss is fastened between said surfaces, said holder having the floss fastened therein is manipulated by a hand in lieu of winding the floss around a finger for teeth cleaning.

14. The holder of claim 13, further comprising second fastening means for fastening the floss therein so that when said jaws are locked together by said locking means, the floss is fastened in said internal surfaces and in said second fastening means.

15. The holder of claim 14, wherein said locking means comprises a locking member, an inner surface, and two separate outer surfaces, said second fastening means including said inner surface and said outer surfaces, said inner surface formed on said locking member, one of said outer surfaces formed on one of said jaws and the other of said outer surfaces formed on the other of said jaws, said outer surfaces combined together being engageable with said inner surface to lock said jaws so that the floss is fastened between said inner surface and at least one of said outer surfaces.

16. The holder of claim 14, wherein said inner surface is a threaded surface and said outer surfaces combined together form a threaded surface.

17. The holder of claim 14, wherein said inner surface is a generally frustum surface and said outer surfaces combined together form a generally uniform surface.

18. The holder of claim 13, wherein said locking means comprises a locking member, an inner surface, and two separate outer surfaces, said inner surface formed on said locking member, one of said outer surfaces formed on one of said jaws and the other of said outer surfaces formed on the other of said jaws, said outer surfaces combined together being engageable with said inner surface to lock said jaws.

19. The holder of claim 13, wherein at least one of said internal surfaces further comprises corrugations formed thereon.

20. The holder of claim 13, wherein each of said jaws comprises a substantially elongated generally semicircular configuration.

21. The holder of claim 13, wherein at least one of said first jaw, said second jaw, and said locking means comprises a substantially ring-shaped configuration adapted to be fitted into a finger.

22. The holder of claim 13, further comprising joining means for joining said jaws at one end thereof.

23. A dental floss device for fastening a length of dental floss, said device comprising:
two separate dental floss holders, each of said holders for fastening each end of the floss, at least one of said holders comprising:
a first jaw having a first internal surface thereon;
a second jaw having a second internal surface thereon, each of said jaws adapted to be handled by fingers, whereby said jaws may be held by fingers to retain the floss, said surfaces being engageable to abut against each other such that the floss is fastened therebetween, whereby the floss is fastened in a manner including at least one of the following: substantially longitudinally therebetween and substantially transversely therebetween; and
locking means for locking said jaws together so that when said jaws are locked together by said locking means, one end of the floss is fastened between said surfaces, whereby when each end of the floss is fastened in each of said holders, each of said holders having the floss fastened therein is manipulated by each hand in a spaced apart relationship for teeth cleaning.

24. The device of claim 23, wherein said at least one of said holders further comprises second fastening means for fastening the floss therein so that when said jaws are locked together by said locking means, the floss is fastened in said surfaces and in said second fastening means.

25. The device of claim 24, wherein said locking means comprises a locking member, an inner surface, and two separate outer surfaces, said second fastening means including said inner surface and said outer surfaces, said inner surface formed on said locking member, one of said outer surfaces formed on one of said jaws and the other of said outer surfaces formed on the other of said jaws, said outer surfaces combined together being engageable with said inner surface to lock said jaws so that the floss is fastened between said inner surface and at least one of said outer surfaces.

26. The device of claim 25, wherein said inner surface is a threaded surface and said outer surfaces combined together form a threaded surface.

27. The device of claim 25, wherein said inner surface is a generally frustum surface and said outer surfaces combined together form a generally uniform surface.

28. The device of claim 23, wherein said locking means of said at least one of said holders comprises a locking member, an inner surface, and two separate outer surfaces, said inner surface formed on said locking member, one of said outer surfaces formed on one of said jaws and the other of said outer surfaces formed on the other of said jaws, said outer surfaces combined together being engageable with said inner surface to lock said jaws.

29. The device of claim 23, wherein at least one of said internal surfaces of said at least one of said holders further comprises corrugations formed thereon.

30. The device of claim 23, wherein each of said jaws of said at least one of said holders comprises a substantially elongated generally semicircular configuration.

31. The device of claim 23, wherein at least one of said first jaw, said second jaw, and said locking means of said at least one of said holders comprises a substantially ring-shaped configuration adapted to be fitted into a finger.

32. The device of claim 23, wherein said locking means of said at least one of said holders comprises a locking member having a generally elongated configuration, such as a cylindrical configuration, adapted to be handled by fingers.

33. The device of claim 23, wherein said at least one of said holders further comprises joining means for joining said jaws at one end thereof.

34. A method of fastening one end of a dental floss in a dental floss holder, which comprises the steps of:

retaining one end of the floss between a first internal surface of a first jaw and a second internal surface of a second jaw of said holder, whereby the floss is retained in a manner including at least one of the following: substantially longitudinally therebetween and substantially transversely therebetween; and locking said jaws together so that said surfaces engageably abut against each other to fasten the floss between said surfaces, whereby when the floss is fastened between said surfaces, said holder having the floss fastened therein is manipulated by a hand in lieu of winding the floss around a finger for teeth cleaning.

35. The method of claim 34, wherein the locking step is performed by engaging a locking member with said jaws so that the floss is also fastened between said locking member and at least one of said jaws.

36. The method of claim 34, wherein the locking step is performed by screwing together threaded surfaces so that the floss is also fastened between said threaded surfaces.

37. The method of claim 34, wherein the locking step is performed by engaging a generally frustum surface with a generally uniform surface so that the floss is also fastened between said frustum and uniform surfaces.

* * * * *